United States Patent [19]

Steggles et al.

[11] Patent Number: 4,675,333
[45] Date of Patent: Jun. 23, 1987

[54] N-[4-[ω-(4-ACYL-3-HYDROXYPHENOXY)ALKOXY]-PHENYL]1H-TETRAZOLE-5-CARBOXAMIDES AND USE THEREOF AS ANTI-ALLERGICS

[75] Inventors: David J. Steggles, Bracknell; John P. Verge, Henley-on-Thames, both of England

[73] Assignee: Lilly Industries Limited, London, England

[21] Appl. No.: 678,445

[22] Filed: Dec. 5, 1984

[30] Foreign Application Priority Data

Dec. 16, 1983 [GB] United Kingdom ............... 8333665

[51] Int. Cl.[4] ............ A61K 31/41; C07D 257/04
[52] U.S. Cl. ............................. 514/381; 548/251; 548/253
[58] Field of Search ............... 548/253, 251; 514/381

[56] References Cited

U.S. PATENT DOCUMENTS 4,595,570 1/1986 Goldsworthy ............... 548/253

FOREIGN PATENT DOCUMENTS 28063 5/1981 European Pat. Off. .
56172 7/1982 European Pat. Off. .
80371 6/1983 European Pat. Off. .
83228 7/1983 European Pat.Off. .
2006782 5/1979 United Kingdom .

*Primary Examiner*—Glennon H. Hollrah
*Assistant Examiner*—D. B. Springer
*Attorney, Agent, or Firm*—Robert A. Conrad; Leroy Whitaker

[57] ABSTRACT

There are described compounds of the formula

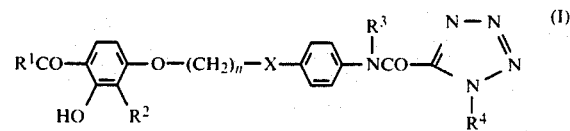

in which $R^1$ is hydrogen or $C_{1-6}$ alkyl, $R^2$ is hydrogen, $C_{1-6}$ alkyl or $C_{3-6}$ alkenyl, $R^3$ is hydrogen or $C_{1-6}$ alkyl, $R^4$ is hydrogen or an N-protecting group, n is 2, 3, 4 or 5, and X is oxygen, sulphur or —$CH_2$—, provided that when X is —$CH_2$— n is 0; and salts thereof. The compounds in which $R^4$ is hydrogen have pharmaceutical activity.

7 Claims, No Drawings

N-[4-[ω-(4-ACYL-3-HYDROXYPHENOXY)ALKOXY]-PHENYL]1H-TETRAZOLE-5-CARBOXAMIDES AND USE THEREOF AS ANTI-ALLERGICS

This invention relates to novel compounds, pharmaceutical compositions containing them and their use as pharmaceuticals.

The compounds of the invention are of the formula

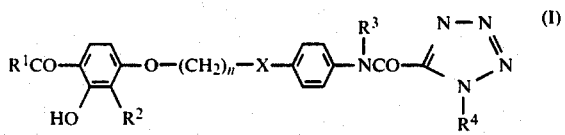

in which $R^1$ is hydrogen or $C_{1-6}$ alkyl, $R^2$ is hydrogen, $C_{1-6}$ alkyl or $C_{3-6}$ alkenyl, $R^3$ is hydrogen or $C_{1-6}$ alkyl, $R^4$ is hydrogen or an N-protecting group, n is 2, 3, 4 or 5, and X is oxygen, sulphur or —$CH_2$—, provided that when X is —$CH_2$— n is 0; and salts thereof.

Compounds of the above formula (I), with the exception of those in which $R^4$ is an N-protecting group which are intermediates in the preparation of the remaining compounds, are inhibitors of leukotriene action, and are thus indicated for use in a variety of pharmacological conditions. For example, they may be used in the prophylactic and therapeutic treatment of immediate hypersensitivity diseases including asthma and in the alleviation of status asthmaticus.

In the above formula (I) reference to a "$C_{1-6}$ alkyl" group includes, for example, methyl, ethyl, propyl, isopropyl and tert. butyl, and is preferably methyl, ethyl or propyl. A "$C_{3-6}$ alkenyl" group includes, for example allyl, isopropenyl, butenyl, isobutenyl and 3-methyl-2-butenyl, and is preferably allyl.

The group $R^4$ can be hydrogen or an N-protecting group. The latter can be any protecting group, such as discussed below appropriate for the reaction in which the tetrazolyl group is added to the diaryl moiety. Such protected tetrazolyl reactants are well known and, for example, are discussed in British Patent No. 2,006,782 and in the chemical literature, for example, J. Med. Chem. (1981), 24, 724. $R^4$ is preferably an optionally substituted benzyl group for example benzyl or p-methoxybenzyl.

A preferred group of compounds of formula (I) is one in which X is oxygen and n is 2, 3, 4 or 5 and preferably $R^1$ is $C_{1-4}$ alkyl, $R^2$ is $C_{1-4}$ alkyl, and $R^3$ and $R_4$ are hydrogen. It is most preferred that $R^1$ and $R^2$ are methyl and propyl, respectively.

Since the compounds of formula (I) bear a tetrazolyl group, an opportunity exists, when $R^4$ is hydrogen, of forming base addition salts, and such salts are included as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms are particularly preferred.

Apart from pharmaceutically acceptable addition salts, other salts are also included within the scope of the invention since they may serve as intermediates in the purification of compounds or in the preparation of other pharmaceutically acceptable salts, or they may be useful for identification, characterization or purification of the free compound.

The pharmaceutical compounds of the invention can be prepared by a process which comprises deprotecting a compound of formula (I) above, in which $R^4$ is an N-protecting group. Thus the present invention includes a process for preparing a compound of the formula

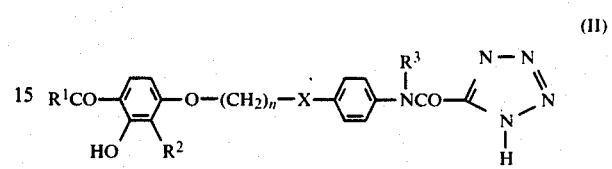

where $R^1$, $R^2$, $R^3$, n and X have the values given above, by reacting a compound of the formula

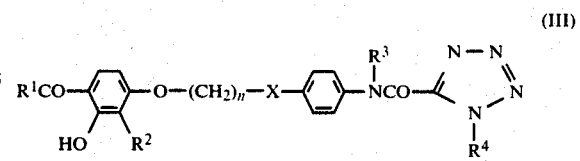

where $R^4$ is an N-protecting group, with acid. The reaction is preferably carried out in acid medium at a temperature of from 0° C. to 100° C., such as for example from 80° C. to 90° C. Acid reactants include, for instance, trifluoroacetic acid, in the presence of anisole, as a catalyst.

Compounds of formula (III) are prepared by reacting an intermediate of the formula

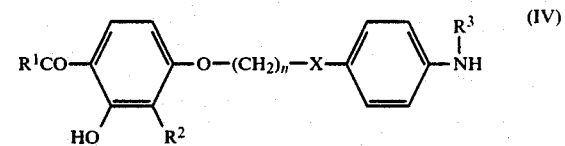

where $R^1$, $R^2$, $R^3$, n and X have the values given above, with an acid chloride of the formula

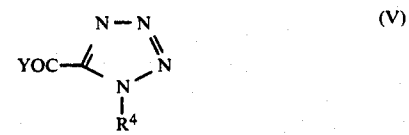

in which $R^4$ is an N-protecting group and Y is halo. The reaction is preferably carried out in an organic solvent, such as for example, dichloromethane, at a temperature of from −10° C. to 30° C., such as for example from 5° C. to 25° C., in the presence of a base, preferably pyridine. The compound of formula (V) is generally prepared in situ by reacting a salt of the formula

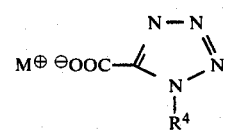

where M⊕ is a monovalent metal cation, preferably one derived from an alkali metal such as a sodium ion or, especially, a potassium ion, with a halogenating agent such as a thionyl halide or oxalyl halide expecially oxalyl chloride, in an organic solvent such as for example toluene and in the presence of a base, preferably pyridine. The reaction can be carried out at a temperature of from −10° C. to 30° C. for example 5° C. to 25° C.

The intermediate of formula (IV) above can be prepared by a sequence of reactions involving, firstly, reaction of the appropriately substituted phenol of the formula

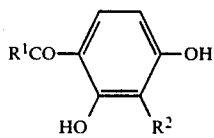

with a haloalkyloxy, haloalkylthio or haloalkyl benzene derivative of the formula

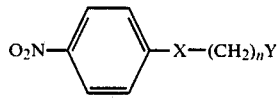

where Y is halo especially chloro, in the presence of a suitable condensing agent such as a combination of sodium hydride and sodium iodide, and with heating.

The product of this reaction, which is of the following formula

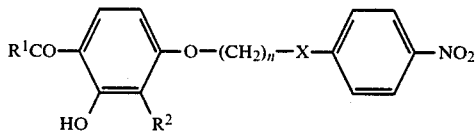

can then be reduced, by conventional means for example by the use of hydrogen and palladium, to give an amine of the formula

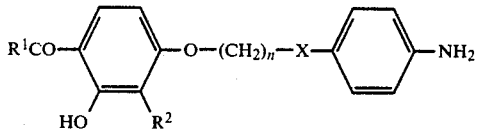

followed by alkylation when it is desired to prepare a compound of formula (IV) in which $R^3$ is alkyl.

As mentioned above, reactants of formula (V) are known compounds described, for example, in British Patent No. 2,006,782, being prepared by reaction of ethyl cyanoformate with the appropriate benzyl azide.

The compounds of the present invention are pharmacologically active, being inhibitors of leukotriene action as shown by the following tests: (a) the in vitro test on guinea pig ileum segments at concentrations of from 10 ng to 50 μg, according to the method of Schild, 1947 Brit. J. Pharm. 2 197-206, using $LTD_4$ as the antagonist (the pharmacological compounds of the following Examples exhibited an $IC_{50}$ against $LTD_4$ of less than $10^{-4}$ molar); (b) the in vivo Guinea Pig Pulmonary Function Test of Austen and Drazen 1974 J. Clin. Invest 53 1679-1685 at intravenous dosage levels of from 0.05 μg to 5.0 mg/kg; and (c) a modified "Herxheimer" test, Journal of Physiology London 117 251 (1952), at doses of from 25 to 200 mg/kg. The "Herxheimer" test is based on an $LTD_4$-induced bronchospasm in guinea pigs which closely resembles an asthmatic attack in man. The compounds also inhibit the formation of leukotrienes, as indicated by their action in the test described by Harvey and Osborne, Journal of Pharmacological Methods 9 147-155 (1983).

The compounds are accordingly indicated for therapeutic use in the treatment of diseases in which leukotrienes are implicated. These include immediate hypersensitivity diseases, allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever.

The compounds may be administered by various routes, for example, by the oral or rectal route, by inhalation, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, and/or enclosed within a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols as a solid or in a liquid medium, ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, more usually 25 to 200 mg, of the active ingredient. The term "unit dosage form" refers to physically discrete units suitable as unit dosges for human subjects and animals, each unit containing a predetermined quantity of active material calculated to produce the desired therapeutic effect, in association with the required pharmaceutical carrier.

The active compounds are effective over a wide dosage range and for example dosage per day will normally fall within the range of 0.5 to 300 mg/kg. and in the treatment of adult humans, more usually in the range of from 5 to 100 mg/kg. However it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Preparations and Examples illustrate the invention.

PREPARATIONS (i)

1-{2-Hydroxy-3-propyl-4-[3-(4-nitrophenoxy)propoxy]phenyl}ethanone

To sodium hydride (6.1 g, 50% dispersion) in dry dimethylformamide (200 ml) was added 2,4-dihydroxy-3-propylacetophenone (24.6 g) in dimethylformamide (20 ml), dropwise with stirring under nitrogen. The resulting solution was heated to 100° C. and 4-nitro-1-(3-chloropropoxy)benzene (27.3 g) and sodium iodide (19.0 g) were added rapidly. The reaction mixture was left to stir over night at 100° C., cooled and evaporated under reduced pressure to a brown oil. The oil was taken up in water, extracted with dichloromethane (×2), washed with aqueous sodium hydroxide (2N), then aqueous sodium thiosulphate, dried over magnesium sulphate, filtered and evaporated under reduced pressure to a dark brown solid. The solid was recrystallised from methanol, with charcoaling, to give pale yellow needles of product, m.p. 98° C.

(ii)

1-{2-Hydroxy-3-propyl-4-[2-(4-nitrophenoxy)ethoxy]phenyl}ethanone

To sodium hydride (1.78 g, 50% dispersion) in dry dimethylformamide (60 ml) was 2,4-dihydroxy-3-propylacetophenone (7.22 g) in dimethylformamide (20 ml), dropwise with stirring under nitrogen. The solution was heated to 100° C. and 4-nitro-1-(2-chdloroethoxy)benzene (7.5 g) and sodium iodide (5.5 g) were added rapidly. The reaction mixture was left to stir at 100° C. for 20 hours, cooled and evaporated under reduced pressure to leave a brown oil. The oil was taken up in water, extracted with dichloromethane (×3), washed with 2N sodium hydroxide (×2), and aqueous sodium thiosulphate, dried over MgSO$_4$, filtered and evaporated under reduced pressure to give a brown solid. The solid was recrystallized twice from methanol to give a yellow crystalline solid, m.p. 124°–125° C.

The following compounds were similarly prepared:
1-{2-Hydroxy-3-propyl-4-[4-(4-nitrophenoxy)butoxy]phenyl}ethanone, m.p. 103°–105° C. (MeOH).
1-{2-Hydroxy-3-propyl-4-[5-(4-nitrophenoxy)pentoxy]phenyl}ethanone, m.p. 98°–100° C. (EtOH).

(iii)

1-{2-Hydroxy-3-propyl-4-[3-(4-aminophenoxy)propoxy]phenyl}ethanone

1-{2-Hydroxy-3-propyl-4-[3-(4-nitrophenoxy)propoxy]phenyl}ethanone (19.6 g) was dissolved in a mixture of ethanol (300 ml) and dimethylformamide (100 ml), to which was added under nitrogen, a slurry of palladium on charcoal catalyst (1.0 g, 5%) in ethanol (50 ml). The suspension was then hydrogenated on a Parr at 60 psi and room temperature for 90 minutes. The suspension was filtered over Celite (registered Trade Mark), washed with ethanol and the filtrate evaporated under reduced pressure to a brown oil, which was triturated with water and filtered to give a brown solid. The solid was recrystallised from ethanol with charcoal to give a white solid, m.p. 75°–77° C.

(iv)

1-{2-Hydroxy-3-propyl-4-[2-(4-aminophenoxy)ethoxy]phenyl}ethanone

1-{2-Hydroxy-3-propyl-4-[2-(4-nitrophenoxy)ethoxy]phenyl}ethanone (6.0 g) was dissolved in a mixture of ethanol (250 ml) and dimethylformamide (60 ml) to which was added, under nitrogen, a slurry of palladium on charcoal (500 mg, 5%) in ethanol (50 ml). The suspension was then hydrogenated on a Parr at 60 psi and room temperature for 2 hours. The suspension was filtered over Celite, washed with ethanol and the filtrate evaporated under reduced pressure to give a brown oil. The oil was triturated with water and filtered to give a brown solid. The solid was recrystallised from ethanol to give a cream solid, m.p. 73°–74° C.

The following compounds were similarly prepared:
1-{2-Hydroxy-3-propyl-4-[4-(4-aminophenoxy)butoxy]phenyl}ethanone.
1-{2-Hydroxy-3-propyl-4-[5-(4-aminophenoxy)pentoxy]phenyl}ethanone, m.p. 70°–72° C. (EtOH).

EXAMPLE 1

N-{4-[3-(4-Acetyl-3-hydroxy-2-propylphenoxy)propoxy]phenyl}-1-(4-methoxyphenylmethyl)-1H-tetrazole-5-carboxamide Potassium 1-(4-methoxyphenylmethyl)-1H-tetrazole-5-carboxylate (10 g) (see British Patent No. 2,006,782) and pyridine (1.8 ml) were stirred together in dry toluene (140 ml) at 10° C. Oxalyl chloride (30.7 ml) was added dropwise and the mixture was stirred at 15° C. for 1 hour. The suspension was filtered and the residual solid washed with dry toluene (100 ml). The filtrate and washings were then evaporated under reduced pressure below 30° C. to give the crude yellow acid chloride which was dissolved in dichloromethane (20 ml) and added dropwise to 1-{2-hydroxy-3-propyl-4-[3-aminophenoxy)propoxy]phenyl}ethanone (12.5 g) and pyridine (2.8 ml) in dry dichloromethane (140 ml) at 10° C. After addition, the mixture was allowed to warm up to 25° C., during a period of 24 hours, washed with water (2×150 ml), then with saturated brine (100 ml), dried over magnesium sulphate, filtered and evaporated under reduced pressure to give a brown solid. The solid was triturated with ether, filtered and recrystallized from acetonitrile to give a pale brown solid, m.p. 122°–125° C.

EXAMPLE 2

N-{4-[2-(4-Acetyl-3-hydroxy-2-propylphenoxy)ethoxy]phenyl}-1-(4-methoxyphenylmethyl)-1H-tetrazole-5-carboxamide Potassium 1-(4-methoxyphenylmethyl)-1H-tetrazole-5-carboxylate (6.28 g) and pyridine (1.1 ml) were stirred in dry toluene (90 ml) at 10° C. Oxalyl chloride (19.3 ml) was added dropwise and the mixture was stirred at 15° C. for 1 hour. The suspension was filtered and the residue was with dry toluene (100 ml). The combined filtrate and washings were evaporated under reduced pressure under 30° C. to give the crude yellow acid chloride which was dissolved in dry dichloromethane (20 ml) and added dropwise to 1-{2-hydroxy-3-propyl-4-[2-(4-aminophenoxy)ethoxy]phenyl}ethanone (7.6 g) pyridine (1.7 ml) in dry dichloromethane (100 ml) at 10° C. After addition the mixture was allowed to warm up to 25° C. for 18 hours, washed with water (2×100 ml), then saturated brine (100 ml), dried over magnesium sulphate, filtered and evaporated under reduced pressure to a pale brown solid. The solid was recrystallised from acetonitrile to give a pale yellow solid, m.p. 123°-225° C.

The following compounds were similarly prepared:
N-{4-[4-(4-Acetyl-3-hydroxy-2-propylphenoxy)butoxy]phenyl}-1-(4-methoxyphenylmethyl)-1H-tetrazole-5-carboxamide, m.p. 111°-113° C. (CH₃CN).
N-{4-[5-(4-Acetyl-3-hydroxy-2-propylphenoxy)pentoxy]phenyl}-1-(4-methxyphenylmethyl)-1H-tetrazole-5-carboxamide, m.p. 107°-110° C. (CH₃CN).

EXAMPLE 3

N-{4-[3-(4-Acetyl-3-hydroxy-2-propylphenoxy)propoxy]phenyl}-1H-tetrazole-5-carboxamide A solution of the 1-(4-methoxyphenylmethyl)tetrazole-5-carboxamide (3.0 g) and anisole (2.2 g) in trifluoroacetic acid (30 ml) was heated for 2 hours at reflux. The cooled solution was evaporated under reduced pressured to leave a brown solid, which was stirred with ether for 30 minutes, filtered and dried to leave a pale brown solid. The solid was recrystallised from ethanol to give a fawn crystalline solid, m.p. 200°-202° C.

EXAMPLE 4

N-{4-[2-(4-Acetyl-3-hydroxy-2-propylphenoxy)ethoxy]phenyl}-1H-tetrazole-5-carboxamide A solution of the 1-(4-methoxyphenylmethyl)tetrazole-5-carboxamide (4.5 g) and anisole (3.3 g) in trifluoroacetic acid (45 ml) was heated at reflux for 2 hours and the solvent was then removed under reduced pressure. The residue was stirred with ether for 30 minutes and filtered to leave a brown solid, which was recrystallised from ethanol to give a fawn crystalline solid, m.p. 201°-203° C.

The following compounds were similarly prepared:
N-{4-[4-(4-Acetyl-3-hydroxy-2-propylphenoxy)butoxy]phenyl}-1H-tetrazole-5-carboxamide, m.p. 190°-191° C. (EtOH).
N-{4-[5-(4-Acetyl-3-hydroxy-2-propylphenoxy)pentoxy]phenyl}-1H-tetrazole-5-carboxamide, m.p. 142°-144° C. (CH₃CN).

The following Examples illustrate the preparation of typical formulations comprising a pharmacologically active compound of the invention.

EXAMPLE 5

| Aerosol | |
| --- | --- |
| Active ingredient | 100 mg |
| Ethanol | 30 ml |
| Propellent 12/114 | q.s. |

The active ingredient is dissolved in ethanol, filled into glass bottles, sealed with a valve (metered to 0.05 ml) and charged with the mixed propellants.

EXAMPLE 6

| Tablet | |
| --- | --- |
| Active ingredient | 100 mg |
| Dried starch | 400 mg |
| Polyvinyl pyrrolidone | 50 mg |
| Sodium carboxymethyl starch | 50 mg |
| Stearic acid | 20 mg |

The active ingredient and starch are mixed together and massed with a solution of polyvinyl pyrrolidone in alcohol. The mass is extruded through a screen, dried, sized and mixed with sodium carboxymethyl starch and stearic acid prior to compression on a tablet machine. Tablets weighing 620 mg are obtained.

EXAMPLE 7

| Capsules | |
| --- | --- |
| Active ingredient | 50 mg |
| Starch flowable | 300 mg |
| Silicone fluid | 5 mg |

A portion of the starch is mixed with the silicone fluid. To the powder is added the active ingredient and the remainder of the starch. This blended mixture is filled into hard gelatin capsules.

We claim:
1. A compound of the formula

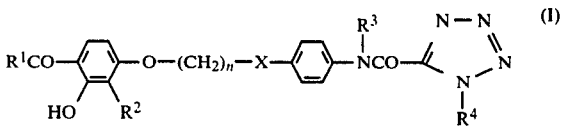

in which R¹ is hydrogen or C₁₋₆ alkyl, R² is hydrogen, C₁₋₆ alkyl or C₃₋₆ alkenyl, R³ is hydrogen or C₁₋₆ alkyl, R⁴ is hydrogen, n is 2, 3, 4 or 5, and X is oxygen or sulphur; or a pharmaceutically acceptable salt thereof.

2. A compound according to claim 1, in which X is oxygen and n is 2, 3, 4 or 5.

3. A compound according to claim 2 in which R¹ is C₁₋₄ alkyl, R² is C₁₋₄ alkyl and R³ is hydrogen.

4. N-{4-[3-(4-Acetyl-3-hydroxy-2-propylphenoxy)propoxy]phenyl}-1H-tetrazole-5-carboxamide.

5. A pharmaceutical formulation comprising a compound according to claim 1 or a pharmaceutically-acceptable salt thereof associated with a carrier or diluent.

6. A method of treating a mammal, including a human, suffering from an immediate hypersensitivity disease, which comprises administering to the mammal an effective amount of a compound as defined in claim 1 or a pharmaceutically-acceptable salt thereof.

7. A compound of the formula

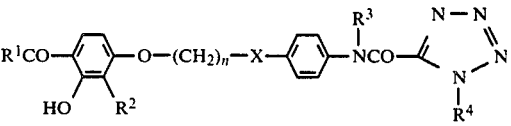

in which R¹ is hydrogen or C₁₋₆ alkyl, R² is hydrogen, C₁₋₆ alkyl or C₃₋₆ alkenyl, R³ is hydrogen or C₁₋₆ alkyl, R⁴ is benzyl or 4-methoxybenzyl, n is 2, 3, 4 or 5, and X is oxygen or sulphur.

* * * * *